United States Patent [19]

Andresen et al.

[11] Patent Number: 4,601,979
[45] Date of Patent: Jul. 22, 1986

[54] PROCESS FOR PREPARING HUMAN INSULIN OR B-30 ESTERS THEREOF

[75] Inventors: Finn H. Andresen, Hillerød; Per Balschmidt, Espergaerde; Kim R. Hejnaes; Hans Kofod, both of Lyngby, all of Denmark

[73] Assignee: Nordisk Insulinlaboratorium, Gentofte, Denmark

[21] Appl. No.: 491,325

[22] PCT Filed: Sep. 14, 1982

[86] PCT No.: PCT/DK82/00082
§ 371 Date: Apr. 11, 1983
§ 102(e) Date: Apr. 11, 1983

[87] PCT Pub. No.: WO83/01074
PCT Pub. Date: Mar. 31, 1983

[30] Foreign Application Priority Data

Sep. 15, 1981 [DK] Denmark .................. 2545/82
Sep. 15, 1981 [DK] Denmark .................. 2546/82

[51] Int. Cl.⁴ .................. C12P 21/00; C12P 21/06; C12P 21/02
[52] U.S. Cl. .................. 435/70; 435/68; 435/69
[58] Field of Search .................. 435/70, 71, 212, 213, 435/68, 69, 262

[56] References Cited

U.S. PATENT DOCUMENTS

| | | | |
|---|---|---|---|
| 3,276,961 | 10/1966 | Bodanszky et al. | 435/71 |
| 3,903,068 | 9/1975 | Ruttenberg | 260/112.7 |
| 4,320,196 | 3/1982 | Morihara et al. | 435/70 |
| 4,320,197 | 3/1982 | Morihara et al. | 435/70 |
| 4,343,898 | 8/1982 | Markussen | 435/70 |

FOREIGN PATENT DOCUMENTS

| | | | |
|---|---|---|---|
| 0017485 | 10/1980 | European Pat. Off. | 435/68 |
| 0017938 | 10/1980 | European Pat. Off. | 435/68 |
| 82/00301 | 2/1982 | PCT Int'l Appl. | 435/68 |
| 2069502 | 8/1981 | United Kingdom | 435/68 |

OTHER PUBLICATIONS

The Condensed Chemical Dictionary, 10th Ed., Revised by G. G. Hawley, p. 564, 1981.
Schmitt et al., Hoppe-Seyler's Z. Physiol. Chem., 359, 799–802 (1978).
Obermeier et al., Hoppe-Seyler's Z. Physiol. Chem., 357, 759–767 (1976).
Morihara et al., Biochem. and Biophys. Research Comm., V92, No. 2, 396–402 (1980).
Morihara et al., Nature, 280, 412–413 (1979).
Masaki et al., Agri. Biol. Chem., 42(7), 1443–1445 (1978).
Gattner et al., Peptides 1980 Proceedings, 372–377 (1981).
Ingalls et al., Biotech. and Bioeng., V.XVII, 1627–1637 (1975).
Homandberg et al., Biochemistry, V. 27, No. 24, 5220–5227 (1978).
Inouye et al., JACS, 101:3, 751–752 (1979).

Primary Examiner—Thomas G. Wiseman
Assistant Examiner—Jayme A. Huleatt
Attorney, Agent, or Firm—Dann Dorfman Herrell and Skillman

[57] ABSTRACT

Human insulin or B-30 esters thereof are prepared by reacting an insulin derivative of the formula

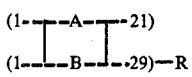

(I)

wherein R is hydroxyl or an amino acid radical being different from threonine, and -A- and -B- represent the A- and B-chains with the same amino acid sequence as in human insulin, with a carboxyl protected and optionally hydroxyl protected L-threonine derivative in a concentration of from 2 to about 6 moles per liter in the presence of trypsin or a trypsin-like enzyme in a reaction medium containing water and optionally also an organic cosolvent at a pH value of from 5 to 9 and at a temperature below 50° C., followed, if desired, by removal of any protecting groups present.

Human insulin is prepared in an easy and simple way in high yield and in high purity.

17 Claims, No Drawings

PROCESS FOR PREPARING HUMAN INSULIN OR B-30 ESTERS THEREOF

TECHNICAL FIELD

The present invention relates to a novel process for the preparation of human insulin or a B-30 ester thereof.

BACKGROUND ART

For many years various insulins have been used in the treatment of insulin-dependent Diabetes. It would be natural to treat human beings with human insulin, which is not possible, however, in view of the existing demand. Therefore, for practical reasons bovine and porcine insulin is used. However, to a larger or smaller extent, these insulins give rise to the formation of antibodies in the human body, which i.a. involves a reduced effect of the further insulin treatment.

This disadvantage is supposed to be caused partly by "impurities" in the bovine/porcine insulin partly by the alien nature. The latter manifests itself therein that the human insulin molecule differs from other animal insulin molecules in a few differences in the composition of amino acid components.

Great improvements have been obtained as regards the insulin preparations after the introduction of the newest purification methods, but the formation of antibodies in the human body can still occur. It is believed that this can be remedied by using human insulin instead of other animal insulin.

It is known to prepare human insulin chemically, vide U.S. Pat. No. 3,903,068 and Hoppe-Seyler's Z. Physiol. Chem. 357, 759-767 (1976).

These processes comprise condensing a desoctapeptide-(B23-30) porcine insulin with a synthetic octapeptide corresponding to the positions B23-30 in human insulin. However, in the first process an alkaline hydrolysis is carried out, which is accompanied by unfavourable side reactions. The second process comprises a nonspecific reaction giving rise to many side reactions and demanding complicated purification procedures. Consequently, these processes are not suitable for use on an industrial scale.

Moreover, U.S. Pat. No. 3,276,961 discloses a process for the preparation of human insulin from other animal insulins by the action of an enzyme, e.g. carboxypeptidase A or trypsin, in the presence of threonine. However, it has not proved to be possible to prepare human insulin to any appreceiable extent by this known process. This is probably due to the fact that trypsin and carboxypeptidase A hydrolyze not only the lysyl-alanine peptide bond (B29—B30), but also other positions in insulin under the working conditions. Trypsin preferably hydrolyzes the arginyl-glycine peptide bond (B22—B23) rather than the lysyl-alanine bond (B29—B30). However, carboxypeptidase A cannot exclusively split off the alanine at the C-terminal of the B-chain without also splitting off asparagine at the C-terminal of the A-chain. It has later been shown that a specific condition, i.e. reaction in an ammonium bicarbonate buffer solution, is necessary in order to hinder the asparagine release, cfr. Hoppe-Seyler's Z. Physiol. Chem., 359, 799-802 (1978). Moreover, a considerable peptide formation scarcely occurs, since the velocity of the hydrolysis reaction is higher than that of the peptide synthesis at the working conditions.

It has later become known that addition of an organic solvent to the reaction medium in an enzymatically catalyzed process remarkably increases the velocity of the peptide bond synthesis and decreases the velocity of the hydrolysis, cfr. Ingalls et al. (1975), Biotechn. Bioeng. 17, 1627, and Homandberg et al., Biochemistry 17, 5220 (1978). The concentration of the solvent in the reaction medium should be high, and in the latter literature passage it is stated that when using 1,4-butanediol as solvent the best results are obtained with a concentration of 80% of said solvent.

Realizing this, desoctapeptide-(B23-B30) insulin (DOI) was successfully coupled by trypsin catalysis with a synthetic octapeptide corresponding to the B23-B30 positions of human insulin using an excess (10:1) of the latter reactant and using an organic solvent (DMF) in a concentration of more than 50%, cfr. J. Am. Chem. Soc. 101, 751-752 (1979). The coupling proceeds with a reasonable yield, but, all things considered, this process is still expensive and cumbersome, because it requires a trypsin catalyzed digestion of porcine insulin to form DOI and, moreover, the required octapeptide must be prepared by a complicated synthesis.

Moreover, Nature 280, 412–413 (1979) and Biochem. Biophys. Res. Com. 92 No. 2, 396–402 (1980) disclose a process for the semisynthetic preparation of human insulin, by which ala-B30 in porcine insulin is exchanged by threonine using trypsin or achromobacterprotease as catalyst. In this process porcine insulin is first hydrolyzed with carboxypeptidase or achromobacterprotease in the presence of $NH_4HCO_3$ to form desalanine-B30 insulin (DAI). The trypsin or achromobacterprotease catalyzed coupling of DAI is carried out using a large excess of a protected threonine derivative, viz. threonine butyl ester (Thr-OBu$^t$) in the ratio of 50:1 to 100:1 and in a high concentration of organic solvent, about 60% of a mixture of dimethylformamide and ethanol. Under such conditions the splitting of the Arg(B22)—Gly(B23) bond is greatly reduced.

It is apparent from the above disclosures that the disadvantages of the process known from U.S. Pat. No. 3,276,961 have been remedied by the reaction being carried out in high concentrations of organic solvents, and it has turned out that the increase in yield is relative to the large content of organic solvent. However, it is still an important feature that one of the reactants is present in a large excess. However, many of the proposed most suitable solvents are suspected of being mutagenic, and as they might be difficult to remove completely from the insulin product, the use of said solvents should be avoided as far as possible.

DISCLOSURE OF THE INVENTION

It is the object of the invention to provide a process for the conversion of an animal insulin, preferably porcine insulin or the desalanine-B30 derivative thereof, into human insulin in a high yield and without using detrimental organic solvents.

It has surprisingly been found that the introduction of threonine in the B30 position in an insulin using trypsin or a trypsin-like enzyme as catalyst proceeds smoothly in an aqueous medium, when the molar concentration of the threonine derivative in the reaction medium is kept above a certain high value.

Accordingly, the present invention relates to a process for the preparation of human insulin or a B-30 ester thereof, in which process a carboxyl and optionally hydroxyl protected L-threonine derivative is reacted with an insulin derivative of the formula

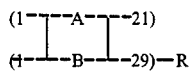 (I)

wherein R is hydroxyl or an amino acid radical being different from the threonine group, and —A— and —B— represent the A- and B-chains with the same amino acid sequence as in human insulin, in the presence of trypsin or a trypsin-like enzyme in a reaction medium containing water and optionally an organic cosolvent at a pH value of from 5 to 9 and at a temperature below 50° C., followed, if desired, by removal of any present protecting groups, and the process of the invention is characterized by the L-threonine derivative being present in the reaction mixture in a molar concentration of from 2 to about 6. The upper limit is dependent on the individual threonine derivative.

The significance of the concentration of the threonine derivative in the reaction medium has not been realized so far. It was believed that the trypsin catalyzed hydrolysis and thereby the byproduct formation in aqueous media were inevitable and that the hydrolysis could only be suppressed by using a medium containing 50-90% of a water-miscible organic solvent.

It has previously been proposed to use a high molar ratio between the L-threonine derivative and the insulin compound, e.g. from 5:1 to 500:1, as the motive power of the process.

It has now been found, in particular in aqueous reactions, that a high molar concentration of a L-threonine derivative in the reaction mixture is of a decisive importance, whereas a large molar ratio between L-threonine derivative and insulin is less important, almost independent of the insulin concentration.

A molar concentration of L-threonine derivative of 2 or more results in a specific reaction of the amino acid with insulin in the B29-B30 position, whereas hydrolysis in the B22-B23 position is suppressed. Moreover, it results in an even very high solubility of the insulin.

The above described process is preferably carried out in an aqueous reaction medium, substantially free of organic cosolvent. When the L-threonine derivative is present in the reaction medium in the above-mentioned high molar concentration, no particular advantages are obtained by further addition of smaller amounts of a water-miscible organic solvent to the reaction mixture. If an organic solvent is added, the addition should be less than about 30% (vol/vol) in order to avoid a decrease of the reaction velocity. In the process of the invention it is preferred to use the L-threonine derivative in the reaction medium in a molar concentration of 3-5. A molar concentration of more than 5 results in a drastic increase of the viscosity of the reaction mixture. A molar concentration of the L-threonine derivative essentially below 2 molar results in increased byproduct formation, decreased solubility of the insulin and corresponding lower yields.

The insulin reactant can be porcine insulin or any derivative thereof of the above indicated formula (I). For example desalanine-B(30) insulin derived from porcine insulin can be used.

The L-threonine reactant is preferably a protected L-threonine derivative of the formula Thr—(R$^1$)(R$^2$)     (II)

wherein Thr is the L-threonine group, R$^1$ is hydrogen or a hydroxyl protecting group, and R$^2$ is a carboxyl protecting group. A preferred L-threonine derivative is an alkyl ester, e.g. a methyl, ethyl or t-butyl ester.

For a possible neutralization of the L-threonine derivative and for adjusting the pH value mineral acids or lower carboxylic acids, e.g. acetic acid or propionic acid, can be used. The proteolytic enzyme should have a specificity for splitting lysine carbonyl bonds in peptides and can e.g. be trypsin from various sources, different trypsin derivatives or achromobacter-protease.

The reaction temperature can be between 0° and 50° C., e.g. between 5° and 20° C.

As a protected L-threonine is used as reactant the insulin product will contain protecting group(s), and said group(s) can be removed in a known manner.

MODES FOR CARRYING OUT THE INVENTION

The process of the invention is further illustrated by means of the following Examples.

EXAMPLE 1

200 mg of porcine insulin were dissolved in 1 ml of a 3.7M aqueous solution of L-threonine ethyl ester, propionate. To this mixture a solution of 4 mg of porcine trypsin in 40µ liters of 0.02M calcium acetate was added, and the pH value was re-adjusted to 6.3 with propionic acid. Thereafter the solution was left at 20° C. for 5 hours, whereafter the reaction was stopped by the addition of 9 ml of water and adjustment of the pH value to 3 with 5N hydrochloric acid.

High pressure liquid chromatographical analysis showed a conversion of 75%.

The reaction mixture was gel filtered on a column of Sephadex ® G-50 Superfine (2.6×90 cm) in 1M acetic acid. The fraction containing human insulin ester and unreacted porcine insulin was freeze-dried.

Yield: 180 mg of product mixture.

Thereafter the product mixture was ion-exchanged at 4° C. on a column of DEAE-cellulose (Whatmann DE-52) (5×2 cm) equilibrated with 75 ml/hour of a buffer consisting of 0.02M TRIS and 7M urea, adjusted to the pH value of 8.1 with hydrochloric acid. After charging of the product the column was eluted for 2.5 hours with the above buffer solution, then for 2 hours with the above buffer in admixture with 0.0045 moles of sodium chloride per liter and at last for 12 hours with the first-mentioned buffer in admixture with 0.011 moles of sodium chloride per liter.

The eluate contained two proteinaceous main fractions. The fraction eluted at first was identified by high pressure liquid chromatography as being human insulin ester and the fraction eluted thereafter as being unreacted porcine insulin.

The main fraction eluted at first was desalted on a column of Sephadex ® G-25 in 0.1M acetic acid and freeze-dried to yield 120 mg of human insulin ethyl ester.

The isolated human insulin ethyl ester was dissolved in 50 ml of water, the pH value being adjusted to 9.5 with 0.1M sodium hydroxide. The solution was left at 25° C. for 72 hours under control of the pH value, whereafter the insulin was crystallized in a manner known per se. Thereby 110 mg of human insulin were obtained, identified by amino acid analysis and high pressure liquid chromatography.

EXAMPLE 2

1 g of L-threonine methyl ester was dissolved in 1 ml of water, whereafter 100 mg of porcine insulin were added, and the mixture was stirred, until the insulin had dissolved. 10 mg of trypsin were dissolved therein, and the mixture was left at ambient temperature for 30 minutes. Then, the reaction was stopped by adjusting the pH value to 3 with 1N hydrochloric acid.

Analysis by high pressure liquid chromatography showed a yield of 24% of human insulin methyl ester.

EXAMPLE 3

1 g of L-threonine methyl ester was dissolved in 1 ml of water. 100 mg of porcine insulin were added and brought into solution with short stirring. In this mixture 10 mg of trypsin were dissolved, and after 5 minutes the pH value of the solution was adjusted to 6.3 by adding 450$\mu$ liters of glacial acetic acid. Thereafter the mixture was left at ambient temperature, and after 2 hours the reaction was stopped by adjusting the pH value to 3 with 1N hydrochloric acid.

Analysis by high pressure liquid chromatography showed a yield of human insulin methyl ester of 31%.

EXAMPLE 4

500 mg of porcine insulin were dissolved in 2.50 ml of 4M L-threonine methyl ester, hydrochloride, pH value: 6.5. After adjustment of the pH value to 6.3 with 300$\mu$ liters of 5N hydrochloric acid a solution of 10 mg of trypsin in 100$\mu$ liters of 0.02M calcium acetate was added, and the reaction mixture was left at 8° C. for 65 hours. Then the reaction was stopped by adding 25 ml of water and adjusting the pH value to 3 with 5N hydrochloric acid.

High pressure liquid chromatographical analysis of the reaction mixture showed a conversion of 43%.

EXAMPLE 5

1.5 ml of a 5M solution of L-threonine methyl ester, acetate containing 200 mg of porcine insulin were prepared by dissolving 200 mg of porcine insulin in 750$\mu$ liters of 10M acetic acid and adding 1 g of L-threonine methyl ester thereto. 2 mg of porcine trypsin were added, and the clear reaction mixture having a pH value of 6.3 was left at 20° C. The reaction was stopped after 90 hours by adding 15 ml of water and adjusting the pH value to 3 with 5N hydrochloric acid.

High pressure liquid chromatographical analysis of the reaction mixture showed a conversion of 85%.

EXAMPLE 6

2 g of zinc-free porcine insulin were dissolved in 200 ml of 0.2M ammonium bicarbonate, adjusted to a pH value of 8.4 with ammonia water. 20 mg of carboxypeptidase A were dissolved in 4 ml of water by means of a few grains of solid TRIS and added to the insulin solution, which was subsequently left at 20° C. for 2.5 hours. The solution was spin-freezed and freeze-dried.

The freeze-dried powder was dissolved in 80 ml of 1M acetic acid and gel filtered on a column packed with Sephadex ® G-50 Superfine (5×90 cm) in the same medium. The insulin-containing fraction was freeze-dried. Hereby 1800 mg of des-(B30-alanine) porcine insulin were obtained.

EXAMPLE 7

A solution of 100 mg of des-(B30-alanine) porcine insulin in 475 $\mu$liters of 3.2M L-threonine methyl ester, acetate, was prepared by dissolving 100 mg of des-(B30-alanine) porcine insulin, prepared according to Example 6, in a mixture of 200 $\mu$liters of water and 75 $\mu$liters of glacial acetic acid and subsequently adding 200 mg of L-threonine methyl ester. After adjustment of the pH value to 6.5 with glacial acetic acid 1 mg of porcine trypsin was added. The mixture was left at ambient temperature for 2 hours, whereafter the reaction was stopped by adding 5 ml of water and adjusting the pH value to 3 with 5N hydrochloric acid.

High pressure liquid chromatographical analysis showed a conversion of 78%.

Working up of the pure human insulin methyl ester and its conversion into human insulin might be carried out by following the directions of Example 1.

EXAMPLE 8

1 g of L-threonine methyl ester was dissolved in 1 ml of water, and 200 mg of desalanine (B-30) porcine insulin prepared according to Example 6 were added to this solution. The pH value of the solution was adjusted to 6.3 with 450 $\mu$liters of glacial acetic acid. 10 mg of trypsin were added, and the solution was left at ambient temperature. After 20 minutes the reaction was stopped by the pH value being adjusted to 3 with 1N hydrochloric acid.

High pressure liquid chromatographical analysis showed a yield of human insulin methyl ester of 73%.

EXAMPLE 9

2 g of L-threonine methyl ester were dissolved in 2 ml of water, and to this solution 400 mg of desalanine (B-30) porcine insulin prepared according to Example 6 were added. The pH value of the solution was adjusted to 6.2 with 900 $\mu$liters of glacial acetic acid. 20 mg of formylated trypsin were added, and the solution was left at ambient temperature for 2 hours. Thereafter, the reaction was stopped by the pH value being adjusted to 3 with 1N hydrochloric acid.

High pressure liquid chromatographical analysis showed a yield of human insulin methyl ester of 69%.

EXAMPLE 10

A reaction mixture containing 200 mg of des-(B-30 alanine) porcine insulin in 1400 $\mu$liters of 2.5M L-threonine methyl ester, acetate was prepared by dissolving 200 mg of des-(B-30 alanine) porcine insulin prepared according to Example 6 in a mixture of 400 $\mu$liters of water and 180 $\mu$liters of glacial acetic acid and subsequent addition of 460 mg of L-threonine methyl ester. To the clear solution a solution of 2 mg of porcine trypsin in 300 $\mu$liters of water was added. The mixture having a pH value of 6.3 was left at 25° C. for 2 hours, whereafter the reaction was stopped by adding 10 ml of water and adjusting the pH value to 3 with 5N hydrochloric acid.

High pressure liquid chromatographical analysis showed a conversion of 64%.

EXAMPLE 11

100 mg of des-B30-alanine porcine insulin prepared according to Example 6 were dissolved in a mixture of 160 $\mu$liters of water, 40 $\mu$liters of absolute ethanol and 75 $\mu$liters of glacial acetic acid, whereafter 200 mg of L-threonine methyl ester were added. To the clear solution having a pH value of 6.5 1 mg of porcine trypsin was added. The mixture was left at ambient temperature for 2 hours, whereafter the reaction was stopped by adding 5 ml of water and adjusting the pH value to 3 with 5N hydrochloric acid.

High pressure liquid chromatographical analysis indicated a yield of 80%.

We claim:

1. A process for the preparation of a B-30 ester of human insulin by reacting a carboxyl protected L-threonine derivative with an insulin derivative of the formula

wherein R is hydroxyl or an amino acid radical being different from threonine, and —A— and —B— represent the A- and B-chains with the same amino acid sequence as in human insulin, in the presence of a proteolytic enzyme, capable of splitting lysine carbonyl peptide bonds, in an aqueous reaction medium substantially free of organic cosolvent, at a pH value of from 5 to 9 and at a temperature below 50° C., and for a time sufficient to accumulate the human insulin ester, wherein the L-threonine derivative is used in the reaction mixture in a concentration of from 2 to about 6 moles/liter.

2. A process of claim 1 wherein the L-threonine derivative is present in the reaction mixture in a concentration of from 3 to 5 moles/liter.

3. A process of claim 1, wherein the insulin derivative used is desalanine-B30 insulin (DAI) derived from porcine insulin.

4. A process of claim 1, wherein the insulin derivative is porcine insulin, R representing alanine.

5. A process of claim 1, wherein the L-threonine derivative is a methyl, ethyl, or t-butyl ester of L-threonine.

6. A process of claim 1, wherein the proteolytic enzyme is trypsin.

7. A process of claim 1, wherein the carboxyl protected L-threonine derivative is also hydroxyl protected.

8. A process of claim 1, wherein any protecting groups present following the reaction of said L-threonine derivative with the said insulin derivative are removed.

9. A process of claim 2, wherein the insulin derivative used is desalanine-B30 insulin (DAI) derived from porcine insulin.

10. A process of claim 2, wherein the insulin derivative is porcine insulin, R representing alanine.

11. A process of claim 2 wherein the L-threonine derivative is a methyl, ethyl or t-butyl ester of L-threonine.

12. A process of claim 2 wherein the proteolytic enzyme is trypsin.

13. A process of claim 3, wherein the L-threonine derivative is a methyl, ethyl, or t-butyl ester of L-threonine.

14. A process of claim 3, wherein the proteolytic enzyme is trypsin.

15. A process of claim 4, wherein the L-threonine derivative is a methyl, ethyl, or t-butyl ester of L-threonine.

16. A process of claim 4, wherein the proteolytic enzyme is trypsin.

17. A process of claim 5, wherein the proteolytic enzyme is trypsin.

* * * * *